(12) United States Patent
Choi et al.

(10) Patent No.: US 9,677,099 B2
(45) Date of Patent: Jun. 13, 2017

(54) RECOMBINANT MICROORGANISMS WITH AN IMPROVED PRODUCTIVITY OF PUTRESCINE AND METHOD FOR PRODUCING PUTRESCINE USING THE SAME

(71) Applicant: CJ CHEILJEDANG CORPORATION, Seoul (KR)

(72) Inventors: Su Jin Choi, Daegu (KR); Hyang Choi, Gyeonggi-do (KR); Min Sun Kang, Jeollanam-do (KR); Sung Hoo Jhon, Seoul (KR); Kyoung Min Lee, Seoul (KR); Hye Won Um, Gyeonggi-do (KR); Young Lyeol Yang, Gyeonggi-do (KR)

(73) Assignee: CJ Cheiledang Corporation, Seoul (KR)

( * ) Notice: Subject to any disclaimer, the term of this patent is extended or adjusted under 35 U.S.C. 154(b) by 117 days.

(21) Appl. No.: 14/372,000

(22) PCT Filed: Jan. 11, 2013

(86) PCT No.: PCT/KR2013/000263
§ 371 (c)(1),
(2) Date: Jul. 11, 2014

(87) PCT Pub. No.: WO2013/105827
PCT Pub. Date: Jul. 18, 2013

(65) Prior Publication Data
US 2015/0104838 A1 Apr. 16, 2015

(30) Foreign Application Priority Data

Jan. 11, 2012 (KR) .................. 10-2012-0003634

(51) Int. Cl.
C12P 13/00 (2006.01)
C12N 1/21 (2006.01)
C12N 9/10 (2006.01)
C12N 15/10 (2006.01)

(52) U.S. Cl.
CPC .......... *C12P 13/001* (2013.01); *C12N 9/1029* (2013.01); *C12N 15/1093* (2013.01)

(58) Field of Classification Search
CPC . C12N 15/1093; C12N 9/1029; C12P 13/001; Y02P 20/52
See application file for complete search history.

(56) References Cited

U.S. PATENT DOCUMENTS

2009/0011478 A1  1/2009 Eppelmann et al.

FOREIGN PATENT DOCUMENTS

| KR | 1020090107920 A | 10/2009 |
| KR | 1020110080475 A | 7/2011 |
| KR | 1020120064046 A | 6/2012 |
| KR | 101174267 B1 | 8/2012 |
| KR | 101188432 B1 | 9/2012 |
| WO | WO 2007/113127 A1 | 10/2007 |
| WO | 2009/125924 A2 | 3/2009 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Zhou et al., Cell Mol Life Sci 63(19-20):2260-2290, 2006.*
Kozak, M., Gene 234:187-208, 1999.*
Altenburger et al., "Polyamine Distribution in Actinomycetes with Group B Peptidoglycan and Species of the Genera *Brevibacterium, Corynebacterium, and Tsukamurella*," International Journal of Systematic Bacteriology 47(2):270-277 (1997).
Schneider et al., "Putrescine production by engineered *Corynebacterium glutamicum*," Appl Microbiol Biotechnol 88:859-868 (2010).
Hwang et al., "Identification of a suppresor gene for the arginine-auxotrophic argJ mutation in Corynebacterium glutamicum," J Ind Microbiol Biotechnol 37:1131-1136, 2010.
Kind et al., "Identification and Elimination of the Competing N-Acetyldiaminopentane Pathway for Improved Production of Diaminopentane by Corynebacterium glutamicum," Applied and Environmental Microbiology 76(15): 5175-5180, 2010.
Qian et al., "Metabolic Engineering of *Escherichia coli* for the Production of Putrescine: A Four Carbon Diamine," Biotechnology and Bioengineering 104:651-662, 2009.

* cited by examiner

*Primary Examiner* — Delia Ramirez

(57) ABSTRACT

The present invention relates to a recombinant microorganism having enhanced ability of producing putrescine at high yield, which is generated by weakening the activity of NCgl1469 in a microorganism of *Corynebacterium* genus that is modified to produce putrescine, and a method for producing putrescine using the same.

11 Claims, 1 Drawing Sheet

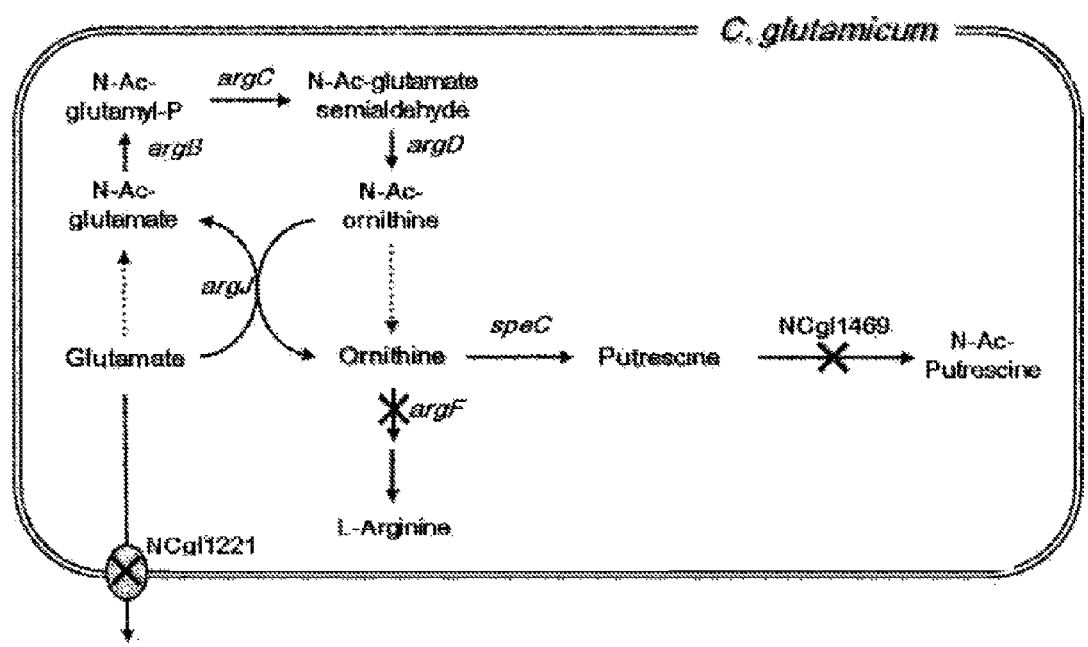

RECOMBINANT MICROORGANISMS WITH AN IMPROVED PRODUCTIVITY OF PUTRESCINE AND METHOD FOR PRODUCING PUTRESCINE USING THE SAME

CROSS-REFERENCES TO RELATED APPLICATIONS

This application is a U.S. national phase application of International PCT Patent Application No. PCT/KR2013/000263, which was filed on Jan. 11, 2013, which claims priority to Korean Patent Application No. 10-2012-0003634, filed Jan. 11, 2012. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_031_00US_ST25.txt. The text file is 33 KB, was created on Nov. 21, 2014, and is being submitted electronically via EFS-Web.

TECHNICAL FIELD

The present invention relates to recombinant microorganisms having an increased productivity of putrescine by modifying the same to weaken the ability to decompose putrescine and a method for producing putrescine using the same.

BACKGROUND ART

Putrescine (or 1,4-butanediamine) is a type of polyamine, such as spermidine and spermine, and is found in gram-negative bacteria and fungi. Since putrescine is present in a wide range of concentrations in various species, it is expected to play an important role in the metabolism of microorganisms. Putrescine is produced mainly by chemical synthesis through acrylonitrile and succinonitrile from propylene. The chemical synthesis uses the substances derived from petrochemicals as starting materials and uses toxic chemicals, and thus it is not environmental-friendly and has a problem of oil depletion.

In order to resolve these problems, there has been much research on developing a method for biosynthesis of putrescine by using microorganisms that is more environmentally-friendly and reduces energy consumption. According to current knowledge, putrescine can be biosynthesized through two pathways from microorganisms. In one pathway, ornithine is produced from glutamate and the ornithine is decarboxylated to synthesize putrescine. In the other pathway, arginine is synthesized from the ornithine, agmatine is produced from arginine, and then putrescine is synthesized from the agmatine. In addition, there are other methods for synthesizing putrescine where the known enzymes involved in the synthetic pathways of putrescine are transformed in a target microorganism. For example, WO09/125,924 discloses a method for producing putrescine at high yield by inactivating the pathway involved in the decomposition and utilization of putrescine present in *E. coli*, by inactivating the pathway in which ornithine, a precursor of putrescine, is converted to arginine, and by enhancing the biosynthetic pathway of ornithine. An article published in 2009 discloses a method for producing putrescine in high concentration by introducing the protein that converts ornithine to putrescine into *Corynebacterium* strains which are not capable of producing putrescine and by enhancing the activity thereof (Qian et al., Biotechnol Bioeng, 104:4, 651-662, 2009).

The produced putrescine can be decomposed by microorganisms or used in other metabolism. For example, spermidine synthase (EC: 2.5.1.16, speE) which is expressed in *E. coli* and *Corynebacterium glutamicum* synthesizes spermidine from putrescine, and acetyltransferase (N-acetyltransferase) which is expressed in *Candida boidinii* acetylates putrescine to N-acetylputrescine. It is known that putrescine can be produced in high concentration in the *E. coli* strain that is modified to have weakened activity of spermidine acetyltransferase (EC: 2.3.1.57. speG) which exhibits high homology with the above acetyltransferase (Korean Patent No. 1188432).

Although the enzyme that acetylates putrescine to N-acetyl putrescine in the microorganism of *Corynebacterium* genus has not been identified yet, it is known that when the gene known to encode NCgl1469, which is a histone acetyltransferase HPA2 and related acetyltransferase, are deleted, the N-acetylation of cadaverine, a type of diamine, is specifically reduced (Kind et al., Appl Environ Microbiol, 76:15, 5175-5180, 2010). However, it was reported that the NCgl1469 does not use putrescine and 1,3-diaminopropane as a substrate. In other words, the NCgl1469 was presumed to have a specific activity only on cadaverine from among all different diamines. On the other hand, it is known that NCgl1469 exhibits the activity of acetyl glutamate synthase and ornithine acetyltransferase in *Corynebacterium glutamicum* to produce ornithine and arginine in high concentration, and when NCgl1469 is overexpressed in the *Corynebacterium glutamicum*, ornithine and arginine can be produced at high yield (Korea Patent No. 1174267). Likewise, the activity of NCgl1469 is specific to glutamate and cadaverine and the effect of NCgl1469 in increasing the productivity of ornithine are known, but it has not been identified yet whether NCgl1469 is associated with the production of putrescine.

DISCLOSURE

Technical Problems

The present inventors identified that putrescine can be produced at high yield by weakening the activity of NCgl1469 in a microorganism of the *Corynebacterium* genus which is modified to produce putrescine, thereby completing the present invention.

Technical Solution

One objective of the present invention is to provide a modified microorganism of *Corynebacterium* genus having enhanced ability to produce putrescine by weakening the activity of NCgl1469 compared to the endogenous activity thereof.

Another objective of the present invention is to provide a method for producing putrescine at high yield using the microorganism of *Corynebacterium* genus.

Advantageous Effect

In the present invention, a *Corynebacterium glutamicum* strain with enhanced ability to produce putrescine is prepared by weakening the activity of NCgl1469 compared to the endogenous activity thereof, and putrescine which is widely used in the industry can be produced in high concentration using the same.

DESCRIPTION OF FIGURES

FIG. 1 is the schematic diagram demonstrating the biosynthetic pathway of putrescine in *Corynebacterium glutamicum* and related genes.

BEST MODE

In order to achieve the above objectives, the present invention provides a modified microorganism of the *Corynebacterium* genus having enhanced ability to produce putrescine, wherein the activity of the NCgl1469 protein having an amino acid sequence represented by SEQ ID NO: 18 or SEQ ID NO: 20 is weakened or removed compared to the endogenous activity thereof.

As used herein, the term "NCgl1469 protein" refers to the protein defined as histone acetyltransferase HPA2 or related acetyltransferase in *Corynebacterium glutamicum*, which have been reported, without the identification of the specific function, to acetylate glutamate and cadaverine (Korean Patent No. 10-1174267, Hwang et al., J Ind Microbiol Biotechnol, 37:11, 1131-1136, 2010, Kind et al., Appl Environ Microbiol, 76:15, 5175-5180, 2010).

The NCgl1469 protein of the present invention comprises the amino acid sequence set forth in SEQ ID NO: 18 or SEQ ID NO: 20. However, it is not limited thereto, since there may be a difference in the amino acid sequence of the protein that exhibits the above activity depending on the microbial species or strains. In other words, it can be a mutein or artificial variant with an amino acid sequence comprising substitution, deletion, insertion, or addition of one or several amino acids at one or more locations of the amino acid sequence of SEQ ID NO: 18 or SEQ ID NO: 20, as long as it can help in increasing the productivity of putrescine by weakening the activity of the protein as proposed in the present invention. Herein, "several" may be different, depending on the location or type in the three-dimensional structure of amino acid residues of the protein, but specifically means 2 to 20, preferably 2 to 10, and more preferably 2 to 5. In addition, the substitution, deletion, insertion, addition or inversion of the amino acid also includes those caused by the natural mutation or artificial variant, if based on the difference in the individual or species of microorganism.

NCgl1469 protein derived from *Corynebacterium glutamicum* ATCC13032 of the present invention has the amino acid sequence set forth in SEQ ID NO: 18, and NCgl1469 protein derived from *Corynebacterium glutamicum* ATCC13869, which has a homology of 99% with the above amino acid sequence, has the amino acid sequence set forth in SEQ ID NO: 20.

The polynucleotide encoding the amino acid sequence in the present invention may comprise the polynucleotide sequence encoding the protein, as long as it has similar activity as NCgl1469 protein of the present invention, with 80% or more, preferably 90% or more, more preferably 95% or more, and particularly preferably 97% or more homology with the amino acid sequence of SEQ ID NO: 18 or SEQ ID NO: 20, and most preferably the polynucleotide sequence set forth in SEQ ID NO: 17 or SEQ ID NO: 19, respectively.

The term "homology" refers to the identity between two amino acid sequences and can be determined by the method well known to those skilled in the art, using BLAST 2.0 to compute parameters such as score, identity and similarity.

In addition, the polynucleotide sequence of the present invention can be hybridized with the polynucleotide of SEQ ID. NO: 17 or SEQ ID. NO: 19 or the probe prepared from the same under "stringent conditions", and can be a variant encoding the protein which normally functions. As used herein, "stringent conditions" refers to the conditions which allow the specific hybridization between the polynucleotide, and described specifically, for example, in Molecular Cloning (A Laboratory Manual, J. Sambrook et al., Editors, 2nd Edition, Cold Spring Harbor Laboratory press, Cold Spring Harbor, N.Y., 1989) or Current Protocols in Molecular Biology (F. M. Ausubel et al., Editors, John Wiley & Sons, Inc., New York), which describes, for example, the hybridization in the hybridization buffer of 65° C. (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate of pH 7. After hybridization, the membrane which DNA is delivered to is cleansed with 2×SSC at room temperature and then cleansed with 0.1 to 0.5×SSC/0.1× SDS at a temperature of 68° C.

In the present invention, the weakening of NCgl1469 activity means that the activity of NCgl1469 is reduced or removed compared to the endogenous activity thereof. The activity of NCgl1469 protein can be weakened by 1) a partial or whole deletion of a polynucleotide encoding the protein, 2) a reduction of the polynucleotide expression by modifying an expression regulatory sequence, 3) a modification of the polynucleotide sequence on chromosome to weaken the activity of the protein or 4) a combination thereof.

In the above method, a partial or whole deletion of a polynucleotide encoding the protein can be performed by substituting the polynucleotide encoding an endogenous target protein in the chromosome for a polynucleotide with a partial deletion of a nucleotide sequence or for a marker gene, with a vector for chromosomal gene insertion. The length of the "partial" deletion is different depending on the type of polynucleotide, but is specifically 2 bp to 300 bp, preferably 2 bp to 100 bp, and more preferably 2 bp to 5 bp.

Also, the reduction of the polynucleotide expression by modifying an expression regulatory sequence can be performed by inducing mutations in the expression regulatory sequence through deletion, insertion, conservative or non-conservative substitution of nucleotide sequence or a combination thereof to further weaken the activity of the expression regulatory sequence, or by replacing the expression regulatory sequence with of the sequence having weaker activity. The expression regulatory sequence includes a sequence encoding promoter, operator sequence, ribosomal binding site and the sequence controlling the termination of transcription and translation.

In addition, the modification of the polynucleotide sequence on chromosome to weaken the activity of the protein can be performed by inducing mutations in the sequence through deletion, insertion, conservative or non-conservative substitution of nucleotide sequence or a combination thereof to further weaken the activity of the sequence, or by replacing the polynucleotide sequence with the modified sequence to have lower activity of the protein.

Meanwhile, a microorganism of *Corynebacterium* genus with enhanced ability to produce putrescine of the present invention can be further modified to weaken the activity of ornithine carbamoyltransferase (ArgF) involved in the synthesis of arginine from ornithine and the activity of protein (NCgl1221) involved in the release of glutamate compared to the endogenous activity thereof for accumulating ornithine, aputrescine precursor, within the cell. In addition, the microorganism of *Corynebacterium* genus can be modified by additionally introducing the activity of ornithine decarboxylase (ODC). Also, the microorganism of *Corynebacterium* genus can be further modified to enhance the activity of acetyl glutamate synthase to convert glutamate to acetyl glutamate, the activity of ornithine acetyltransferase (ArgJ) to convert acetyl ornithine to ornithine, the activity of acetyl glutamate kinase (ArgB) to convert acetyl glutamate to acetyl glutamyl phosphate, the activity of acetyl gamma glutamyl phosphate reductase (ArgC) to convert acetyl glutamyl phosphate to acetyl glutamate semialdehyde, and the activity of acetyl ornithine amino transferase (ArgD) to convert acetyl glutamate semialdehyde to acetyl ornithine, compared to the endogenous activities thereof, thereby enhancing the biosynthetic pathway of ornithine, a putrescine precursor.

In this case, the ArgF, NCgl1221, ODC, ArgC, ArgJ, ArgB and ArgD may have, but are not specifically limited to, the amino acid sequences of SEQ ID. NO: 21, 22, 23, 24, 25, 26, 27, respectively, or the amino acid sequences with 80% or more, preferably 90% or more, more preferably 95% or more, and most preferably 97% or more homology with the same.

As used herein, the term "ornithine decarboxylase (ODC)" refers to an enzyme that produces putrescine using ornithine, and the ODC requires pyridoxalphosphate (Pyridoxal 5'-phosphate, PLP) as a coenzyme, is present in most Gram-negative bacteria and may be present in some of the intestinal bacteria such as *Lactobacillus* of Gram-positive bacteria. *E. coli* has two types of genes encoding ODC, one of which, speC, is expressed continuously at the certain concentration and the other, speF, is induced to be expressed under specific conditions (the presence of ornithine at higher than certain concentrations and low pH). Depending on species, some species, like *E. coli*, have two kinds of ODC, and others have only one type. The species such as *Escherichia* sp., *Shigella* sp., *Citrobacter* sp., *Salmonella* sp., and *Enterobacter* sp. have two kinds of ODC (speC, speF), and the strains of *Yersinia* sp., *Klebsiella* sp., *Erwinia* sp., have one kind of ODC (speC). In case of *lactobacillus*, ODC is expressed in one type of gene (speF), and is known to be induced to be expressed under the conditions of low pH or abundant ornithine and histidine.

ODC activity can be introduced to the recombinant microorganism of *Corynebacterium* genus of the present invention using genes encoding ODC derived from the various species.

The polynucleotide encoding ODC may include, but is not limited to, the polynucleotide encoding the protein consisting of the amino acid sequence of SEQ ID NO: 23 of the amino acid sequence with 70% or more, preferably 80% or more preferably 90% or more homology with the same.

In addition, the introduction of ornithine decarboxylase (ODC) activity to the microorganisms can be performed by the various methods well known in the art, and, for example, the method to insert the polynucleotide consisting of a nucleotide sequence encoding ODC to chromosome, the method to introduce the polynucleotide to the microorganisms by introducing to the vector system, the method to insert the polynucleotide consisting of a nucleotide sequence encoding ODC and promoter with improved activity or the modification to the upper region of nucleotide sequence encoding ODC and the method to insert the polynucleotide which is introduced the mutation of the nucleotide sequence encoding ODC can be used, and more preferably, if the nucleotide sequence encoding ODC is introduced, known CJ7 promoter can be used as a promoter to control the expression of the same.

In addition, the enhancement of the activity of ArgC, ArgJ, ArgB and ArgD can be achieved by 1) an increase of the copy number of polynucleotide encoding the enzyme, 2) a modification of the expression regulatory sequence to increase the polynucleotide expression, 3) a modification of the polynucleotide sequence on chromosome to enhance the activity of the enzyme or 4) a combination thereof.

In method 1), the increase of the copy number of polynucleotide encoding the enzyme can be achieved by operably linking the polynucleotide to the vector or by inserting the same to the chromosome of the host cell. More specifically, the copy number of polynucleotide of the host cell can be increased by introducing a vector that is capable of replicating and functioning independently, wherein the polynucleotide encoding the enzyme of the present invention is operably linked, or by introducing the vector capable of inserting the polynucleotide into the chromosome of the host cell, wherein the polynucleotide is operably linked.

As used herein, the term "vector" refers to the DNA construct consisting of the nucleotide sequence of the polynucleotide encoding the target protein operably linked to the proper regulatory sequence to express the target protein in the proper host. The regulatory sequence includes the promoter which can initiate transcription, any operator sequence to control the transcription, the sequence to encode the appropriate mRNA ribosome binding site, and the sequence to control the termination of transcription and translation. The vector can be transfected into a suitable host, and then can be replicated or can function independently from the host genome, and can be integrated into the genome itself.

In the present invention, any vector which can be replicated in the host can be used without any specific limitation as long as it is known in the art. Examples of commonly used vectors are plasmid, cosmid, virus and bacteriophage in natural state or recombinant state. For example, pWE15, M13, λMBL3, λMBL4, λIXII, λASHII, λAPII, λt10, λt11, Charon4A, and Charon21A can be used as a phage vector or cosmid vector, and pBR system, pUC system, pBluescriptII system, pGEM system, pTZ system, pCL system and pET system can be used as a plasmid vector. The vector which can be used in the present invention is not particularly limited and the known expression vectors can be used. Preferably, pACYC177, pACYC184, pCL, pECCG117, pUC19, pBR322, pMW118, pCC1BAC vectors can be used. Most preferably, pACYC177, pCL, pCC1BAC vectors can be used.

In addition, the vector which can insert the polynucleotide encoding the target protein by being transformed into a host cell may preferably be, for example, a shuttle vector, pECCG112 (Korean Patent Publication No. 1992-0000933) which is able to replicate by itself both in *E. coli* and *Coryneform* bacteria, but is not limited thereto.

In addition, the polynucleotide encoding the target protein in the chromosome can be replaced by a new polynucleotide by using a vector for chromosomal gene insertion. The insertion of the polynucleotide to the chromosome can be achieved by any method known in the art, for example, by homologous recombination. Since the vector of the present invention may be inserted into the chromosome by inducing a homologous recombination, the selection marker may be additionally included to confirm a successful gene insertion into the chromosome. A selection marker is for screening the cells which are transformed with the vector, in other words, for determining whether the target polynucleotide is inserted. The markers that can provide selectable phenotypes such as drug resistance, auxotrophy, resistance to toxic agents or expression of surface proteins may be used. In an environment treated with a selective agent, only the cells expressing the selection marker can survive or cells with a different phenotype will appear, and thus the successfully transformed cells can be selected through this method.

As used herein, the term "transfection" refers to the introduction of the vector comprising a polynucleotide encoding the target protein into the host cell so that the protein which the polynucleotide encodes can be expressed. The transfected polynucleotide includes all polynucleotides which encode target proteins that can be expressed in the host cell regardless of the location, whether it is inserted into the chromosome of the host cell or located outside the chromosome. In addition, the polynucleotide includes DNA and RNA encoding the target protein. The polynucleotide can be introduced in any form as long as it can be introduced into the host cell and expressed. For example, the polynucleotide can be introduced into a host cell in a form of an expression cassette which is gene construct, comprising all the required elements for self-expression. The expression cassette typically includes a promoter operably linked to the polynucleotide, transcription termination signal, ribosomal binding site, and translation termination signal. The expression cassette may be the form of expression vector capable of self-replication. In addition, the polynucleotide may be introduced into a host cell in its own form and operably linked to the sequences required for the expression of host cell.

As used herein, the term "operably linked" refers to the functional connection between the promoter sequence initiating or mediating the transcription of polynucleotide encoding the target protein and the polynucleotide.

In addition, the method 2) modification of the expression regulatory sequence to increase the expression of the polynucleotide in the present invention can be performed by inducing the mutation of the sequence through deletion, insertion, conservative or non-conservative substitution of nucleotide sequence or a combination thereof, or by substitution by the nucleotide sequence with enhanced activity. The expression regulatory sequence includes promoter, operator sequence, sequence encoding ribosomal binding sites, and sequence to control the termination of transcription and translation.

A strong heterologous promoter can be linked to the upper of expression unit of the polynucleotide instead of original promoters and an example of a strong promoter is pcj7 promoter, lysCP1 promoter, EF-Tu promoter, groEL promoter, aceA or aceB promoter, etc., and more preferably lysCP1 promoter or pcj7 promoter derived from *Corynebacterium* is operably linked to enhance the expression of polynucleotide encoding the enzyme. Herein, lysCP1 promoter, which is an improved promoter through substitution of the nucleotide sequence of the promoter region of polynucleotide encoding aspartate kinase and aspartate semialdehyde dehydrogenase, is strong enough to increase the activity of the corresponding enzyme by 5 times compared to the wild type through enhancement of expression of aspartate kinase gene (International Patent Publication No. 2009-096689). In addition, the pcj7 promoter was identified to be expressed in *Corynebacterium ammoniagenes* and *Escherichia* and to have a strong promoter activity, in searching the area with strong promoter sequence of *Corynebacterium ammoniagenes*, and can be expressed in *Corynebacterium glutamicum* as well in high intensity (Korean Patent No. 0620092).

In addition, the method 3) modification of the polynucleotide sequence on chromosome encoding the enzyme of the present invention can be performed by inducing the mutation of the sequence through deletion, insertion, conservative or non-conservative substitution of nucleotide sequence or a combination thereof to enhance the activity of the sequence, or by substitution by the nucleotide sequence with enhanced activity.

The microorganism in the present invention, which is a microorganism with enhanced ability to produce putrescine, includes prokaryotic microorganism, wherein the protein with amino acid sequence set forth in SEQ ID NO: 18 or SEQ ID NO: 20 is expressed, and may be, for example, the microorganism of *Escherichia* sp., *Shigella* sp., *Citrobacter* sp., *Salmonella* sp., *Enterobacter* sp., *Yersinia* sp., *Klebsiella* sp., *Erwinia* sp., *Corynebacterium* sp., *Brevibacterium* sp., *Lactobacillus* sp., *Sllenomanas* sp., and *Vibrio* sp.

The microorganism in the present invention is preferably the microorganism of *Corynebacterium* genus and may be more preferably be of *Corynebacterium glutamicum*.

In one example of the present invention, the microorganism of *Corynebacterium* genus of accession number KCCM11138P (Korean Patent Publication No. 2012-0064046), which has the ability to produce putrescine of a high concentration through enhanced putrescine-generating pathway, was mutated. Specifically, the putrescine-producing strain KCCM11138P is the putrescine-overproducing strain, wherein the gene encoding ornithine carbamoyltransferase (ArgF) for accumulating ornithine and the gene encoding glutamate exporter (NCgl1221) for increasing intracellular glutamate are deleted from ATCC13032 strains, the gene encoding ornithine decarboxylase (speC) is introduced, and the expression level of ornithine biosynthesis genes (argCJBD) is increased.

In another example of the present invention, *Corynebacterium glutamicum* ATCC13869 based putrescine-producing strain DAB12-a based on the same genotype as the KCCM11138P was mutated. Specifically, putrescine-producing strain DAB12-a comprising ATCC13869 strain obtained from American Type Culture Collection (ATCC), wherein the gene encoding ornithine carbamoyltransferase (ArgF) and the gene encoding the protein NCgl1221 to release glutamate are deleted, the gene (speC) encoding ornithine decarboxylase (ODC) derived from *E. coli* is introduced, and the promoter of ornithine biosynthesis gene operon (argCJBD) is replaced with the improved promoter.

In an example of the present invention, *Corynebacterium glutamicum* strain with an enhanced ability to produce putrescine was prepared by weakening or removing the activity of NCgl1469 protein set forth in SEQ ID NO: 18 in the microorganism of *Corynebacteriumglutamicum* KCCM11138P (Korean Patent Publication No. 2012-0064046), with an ability to produce putrescine of a high concentration by deletion of argF and NCgl1221, introduction of speC and enhancement of argCJBD (refer to FIG. 1).

The strain with the activity of NCgl1469 protein deleted was named *Corynebacterium glutamicum* CC01-0163, deposited in Korean Culture Center of Microorganisms (hereinafter, referred as "KCCM") as a consignment number of KCCM11240P as of Dec. 26, 2011. The result of culturing the strain showed that N-acetyl putrescine is not produced, the productivity of putrescine is improved with the improvement level similar as the level of non-produced N-acetyl putrescine, and therefore NCgl1469 has the activity to acetylate putrescine.

In addition, *Corynebacterium glutamicum* strain, DAB12-aΔNCgl1469, with an enhanced ability to produce putrescine was prepared by eliminating the activity of NCgl1469 protein set forth in SEQ ID NO: 20 in the putrescine-producing strain DAB12-a, and the result of culturing the strain showed that N-acetyl putrescine is not produced and the productivity of putrescine is increased.

Meanwhile, the present invention relates to the method for producing putrescine comprising culturing the microorganism of *Corynebacterium* genus with enhanced ability to produce putrescine, wherein the activity of NCgl1469 protein consisting of the amino acid sequence set forth in SEQ ID NO: 18 or SEQ ID NO: 20 is weakened; and isolating putrescine from the obtained culture.

The culturing process in the present invention may consist of the appropriate medium and culturing conditions known in the art. Those skilled in the art can easily adjust and use the culturing process according to selected strains. Example of the culturing process includes use of batch, continuous and fed-batch cultures, but is not limited thereto. The culture medium used must appropriately satisfy the requirements for a specific strain.

The culture medium used must appropriately satisfy the requirements of specific strains. Culture media for various microorganisms are known (for example, "Manual of Methods for General Bacteriology" from American Society for Bacteriology (Washington D.C., USA, 1981)). As a source of carbon in the medium, sugar and carbohydrates (e.g., glucose, sucrose, lactose, fructose, maltose, molasses, starch, and cellulose), butterfat and fat (e.g., soybean oil, sunflower seed oil, peanut oil and coconut oil), fatty acid (e.g., palmitic acid, stearic acid and linoleic acid), alcohol (e.g., glycerol and ethanol) and organic acid (e.g., acetic acid), etc. can be used. These substances can be used individually or as a mixture. As a source of nitrogen, nitrogen-containing organic compound (e.g., peptone, yeast extract, beef extract, malt extract, corn steep liquor, soybean meal powder and urea) or inorganic compound (e.g., ammonium sulfate, ammonium chloride, ammonium phosphate, ammonium carbonate and ammonium nitrate) can be used and these substances also can be used individually or as a mixture. As a source of phosphorus, potassium dihydrogen phosphate or dipotassium hydrogen phosphate or the corresponding sodium-containing salt can be used. In addition, the culture medium may comprise metal salt (e.g., magnesium sulfate or iron sulfate) which is essential for the growth, and finally, essential growth-promoting substances such as amino acids and vitamins, may be used in addition to the above-mentioned substances. The appropriate precursor may be added in addition to the culture medium. The feed substance can be provided in the culture all at once or adequately during culturing.

The pH of the culture can be adjusted by a proper use of basic compound (e.g., sodium hydroxide, potassium hydroxide or ammonia) or acidic compound (e.g., phosphoric acid or sulfuric acid). Foaming can be adjusted using the foaming agent such as fatty acid polyglycolester. Aerobic condition can be maintained by introducing oxygen or oxygen-containing gas mixtures, for example, air into the culture. Culturing temperature is typically 20 to 45° C., preferably 25 to 40° C. Culturing is continued until the generation of putrescine reaches the desired maximum. This goal is usually achieved in 10 to 160 hours. Putrescine may be released into culture medium, or contained in the cell.

For the method for collecting and gathering the produced putrescine in the culturing process of the present invention, the target substance can be collected from the culture medium using the appropriate known method in the art depending on the culture method, for example, batch, continuous or fed-batch culture method.

MODE FOR INVENTION

Hereinafter, the present invention will be described in more detail with reference to Examples. However, these Examples are for illustrative purposes only, and the invention is not intended to be limited by these Examples.

Example 1

Strain with Removed NCgl1469 Activity

Example 1-1

Preparation of NCgl1469-Deleted Strain Based on a Putrescine-Producing Strain ATCC13032

In order to block the synthetic pathway of N-acetyl putrescine from putrescine in the cell, a mutant strain wherein the gene encoding NCgl1469 is deleted was prepared, on the basis of the microorganism of *Corynebacterium* genus having the ability to produce putrescine (KCCM11138P(ATCC13032ΔargFΔNCgl1221P(CJ7)-argCJBDbioAD::P(CJ7)-speC(Ec)) disclosed in the patent application of the present inventors (Patent Publication No. 2012-0064046), which is prepared by deleting the endogenous gene encoding ornithine carbamoyltransferase(ArgF) and the endogenous gene encoding glutamate exporter (NCgl1221) which is involved in the release of glutamate, by introducing the gene encoding ornithine decarboxylase (SpeC) derived from a wild type *E. coli* W3110 into the chromosome, and by substituting a promoter of argCJBD gene group encoding the enzyme involved in the synthesis of ornithine from glutamate, in a wild type *Corynebacterium glutamicum* strain ATCC13032.

Specifically, NCgl1469-del-F1_BamHI and NCgl1469-del-R1_SalI were prepared as primers for obtaining a homologous recombinant fragment of N-terminal domain of NCgl1469, and NCgl1469-del-F2_SalI and NCgl11469-del-R2_XbaI were prepared as primers for obtaining a homologous recombinant fragment of C-terminal domain of NCgl1469, on the basis of nucleotide sequence of the gene NCgl469 of ATCC13032 strain (SEQ ID. NO: 17) (Table 1).

TABLE 1

Primers for the production of NCgl1469 deleted strain based in ATCC13032

| | |
|---|---|
| NCgl1469-del-F1_BamH1 (SEQ ID NO: 1) | CGGGATCCAACCTTCAGAACGC GAATAC |
| NCgl1469-del-R1_SalI (SEQ ID NO: 2) | CGCGTCGACTTGGCACTGTGAT TACCATC |
| NCgl1469-del-F2_SalI (SEQ ID NO: 3) | CGCGTCGACTTGGGTTATATCC CCTCAGA |
| NCgl1469-del-R2_XbaI (SEQ ID NO: 4) | TGCTCTAGATAGTGAGCCAAGA CATGGAA |

In order to obtain N-terminal fragment and C-terminal fragment of NCgl1469 gene, PCR was performed using a set of primers (NCgl1469-del-F1_BamHI & NCgl1469-del-R1_SalI, and NCgl1469-del-F2_SalI & NCgl1469-del-R2_XbaI) and the chromosome of ATCC13032 strain as a template. PCR reaction was performed with 30 cycles of denaturation at 95° C. for 30 seconds, annealing at 53° C. for 30 seconds, and elongation at 72° C. for 30 seconds.

After running the PCR products on 0.8% agarose gel electrophoresis, a DNA band of target size was isolated and purified. Then, the PCR product of N-terminal domain and PCR product of C-terminal domain were treated with BamHI&SalI and SalI&XbaI respectively, and then cloned into the pDZ vector treated with BamHI&XbaI. The resulting plasmid to be used for NCgl1469 deletion was named as pDZ-NCgl1469 (K/O).

In order to generate KCCM11138PΔNCgl1469 strain, the above-prepared pDZ-NCgl1469(K/O) vector was introduced to KCCM11138P strain through electroporation and plated on a BHIS medium plate (Brain heart infusion 37 g/L, sorbitol 91 g/L, and agar 2% per 1 L) containing kanamycin (25 μg/ml).

Successful insertion of the vector to the chromosome was confirmed by observing blue color in the solid medium containing 5-bromo-4-chloro-3-indolyl-β-D-galactoside (X-gal). The strains with single crossover were cultured with shaking in a nutrient medium (30° C., 8 hours), and each of them was serially diluted from $10^{-4}$; to $10^{-10}$ and plated on a solid medium containing X-gal. While majority of colonies appeared as blue colony, a low proportion of colonies appeared as white colonies, and by selecting the white colonies, the NCgl1469 gene-deleted strains with double crossover were finally selected. A successful knockout of the gene in the strain was confirmed by PCR using the primers, NCgl1469-del-F1_BamHI and NCgl1469-del-R2_XbaI. The strain confirmed by PCR was named as KCCM11138PΔNCgl1469.

Example 1-2. Preparation of NCgl1469-Deleted Strain Based on a Putrescine-Producing Strain ATCC13869

Using the same method used for producing the putrescine-producing strain KCCM11138P based on *Corynebacterium glutamicum* ATCC13032, another putrescine-producing strain was prepared in the present Example, on the basis of *Corynebacterium glutamicum* ATCC13869, by deleting the endogenous gene encoding ornithine carbamoyltransferase (ArgF) and the endogenous gene encoding glutamate exporter (NCgl1221) which is involved in the release of glutamate, by introducing the gene encoding ornithine decarboxylase (SpeC) derived from wild type *E. coli* W3110 into the chromosome, and by substituting the promoter of argCJBD gene group encoding the enzyme involved in synthesis of ornithine from glutamate. The prepared putrescine-producing strain was named as DAB12-a (argF-deleted, NCgl1221-deleted, *E. coli* speC-introduced, and arg operon promoter-substituted strain), and NCgl1469-deleted strains were prepared based on the same.

To be specific, in order to identify the gene encoding NCgl1469 derived from *Corynebacterium glutamicum* ATCC13869 and the amino acid sequence of the protein expressed there from, PCR was performed using the genomic DNA of *Corynebacterium glutamicum* ATCC13869 as a template and a set of primers, SEQ ID NO: 5 and 6 (NCgl1469-F and NCgl11469-R) (Table 2). Here, PCR reaction was performed with 30 cycles of denaturation at 95° C. for 30 seconds, annealing at 53° C. for 30 seconds, and elongation at 72° C. for 30 seconds. The PCR products were separated by electrophoresis and their sequences were analyzed. Through sequence analysis, it was identified that the gene encoding NCgl1469 derived from *Corynebacterium glutamicum* ATCC13869 comprises a nucleotide sequence represented by SEQ ID NO: 19 and the encoded protein comprises an amino acid sequence represented by SEQ ID NO: 20. When the amino acid sequences of NCgl1469 derived from *Corynebacterium glutamicum* ATCC13032 and that of NCgl1469 derived from *Corynebacterium glutamicum* ATCC13869 were compared, they showed 99% sequence homology.

TABLE 2

| Primer to identify the gene coding ATCC1369 derived NCgl1469 | |
| --- | --- |
| NCgl1469-F (SEQ ID NO: 5) | CATCCTGGGGAATTCATTTGTCAT |
| NCgl1469-R (SEQ ID NO: 6) | GGCGTTCGACAAAGCCTAATAAG |

In order to delete the gene encoding NCgl469 derived from *Corynebacterium glutamicum* ATCC13869, a plasmid named pDZ-2'NCgl1469(K/O) was prepared. First, the N-terminal domain and C-terminal domain of NCgl1469 gene were amplified by PCR using a genomic DNA of *Corynebacterium glutamicum* ATCC13869 as a template and two pairs of primers listed in Table 3 as described in Example <1-1>. Then the PCR products of N-terminal and C-terminal domains were restriction digested with BamHI&SalI and SalI&XbaI respectively and then cloned into the pDZ vector digested with BamHI&XbaI, thereby generating a plasmid pDZ-2'NCgl1469 (K/O).

TABLE 3

| Primers for the production of NCgl1469 deleted strain based in ATCC13869 | |
| --- | --- |
| 2'NCgl1469-del-F1_BamHI (SEQ ID NO: 7) | CGGGATCCGTGGCTG CCAGGAATGGCTCC |
| NCgl1469-del-H1-SAlI (SEQ ID NO: 2) | CGCGTCGACTTGGCA CTGTGATTACCATC |
| NCgl1469-del-F2_SalI (SEQ ID NO: 3) | CGCGTCGACTTGGGT TATATCCCCTCAGA |
| 2'NCgl1469-del-R2_XbaI (SEQ ID NO: 8) | TGCTCTAGACCCAAA ACATCCTGGCGGC |

The plasmid pDZ-2'NCgl1469(K/O) was transfected into *Corynebacterium glutamicum* DAB12-a using the same as in Example <1-1> and the strain wherein the gene encoding NCgl1469 is deleted was selected. The selected *Corynebacterium glutamicum* mutant strain was named DAB12-aΔNCgl1469.

Example 2

The Strain with Weakened Activity of NCgl1469

In order to weaken the synthetic pathway of N-acetyl putrescine from putrescine in a microorganism of *Coryne-*

*bacterium* genus KCCM11138P that is capable of producing putrescine (Korean Patent Publication No. 2012-0064046), a strain with substitution of a start codon of NCgl1469 was prepared.

To be specific, based on the nucleotide sequence of NCgl1469 derived from ATCC13032 strain, a set of primers, NCgl1469-gtg-F1 and NCgl1469-gtg-R1, were prepared to obtain a homologous recombinant fragment of the N-terminal domain of NCgl1469, and a set of primers, NCgl1469-gtg-F2 and NCgl1469-gtg-R2, were prepared to obtain a homologous recombinant fragment of the C-terminal domain of NCgl1469 (Table 4). The site where the N-terminal fragment and C-terminal fragment are combined was designed such that a start codon of NCgl1469, ATG, is substituted by GTG.

TABLE 4

Primer to produce a strain with substitution of the initiation codon in NCgl1469

| | |
|---|---|
| NCgl1469-gtg-F1 (SEQ ID NO: 9) | CGGGATCCTGGATTGTATACTGCGACCAC |
| NCgl1469-gtg-R1 (SEQ ID NO: 10) | CAAACGGTGGGACTCACGGATACCAGAATAGC |
| NCgl1469-gtg-F2 (SEQ ID NO: 11) | GCTATTCTGGTATCCGTGAGTCCCACCGTTTTG |
| NCgl1469-gtg-R2 (SEQ ID NO: 12) | TGCTCTAGATTAAACAGTTGGCATCGCTGG |

In order to obtain the N-terminal fragment and C-terminal fragment of NCgl1469 gene of ATCC13032 strain, PCR was performed using two sets of primers (NCgl1469-gtg-F1 & NCgl1469-gtg-R1 and NCgl1469-gtg-F2 & NCgl1469-gtg-R2) and the chromosome of ATCC13032 strain as a template. PCR reaction was performed with 30 cycles of denaturation at 95° C. for 40 seconds, annealing at 52° C. for 40 seconds, and elongation at 72° C. for 30 seconds using a pfu polymerase (Stratagene).

After performing electrophoresis of the PCR products on 0.8% agarose gel, a DNA band of target size was isolated and purified. Then the PCR products of the N-terminal domain and C-terminal domain of NCgl1469 gene of ATCC13032 strain were each fusion-cloned into a pDZ vector digested with BamHI&XbaI. For fusion cloning, In-Fusion HD Cloning Kit (Clontech) was used. The prepared plasmid to be used for substitution of NCgl1469 start codon was named as pDZ-NCgl1469 (gtg).

In order to obtain a KCCM11138P NCgl1469(gtg) strain, the prepared pDZ-NCgl1469(gtg) vector was introduced into KCCM11138P strain through electroporation and the transformed cells were plated on a BHIS medium plate (Brain heart infusion 37 g/L, sorbitol 91 g/L, agar 2%, 1 L basis) containing kanamycin (25 µg/ml). Successful insertion of the vector into the chromosome of strain was confirmed by observing blue colonies in the solid medium containing 5-bromo-4-chloro-3-indolyl-β-D-galactoside (X-gal). The strains with single crossover were cultured with shaking in a nutrient medium (30° C., 8 hours), and each of them was serially diluted from $10^{-4}$ to $10^{-10}$ and plated on a solid medium containing X-gal. While the majority of the colonies appeared as blue colonies, a low proportion of colonies appeared as white colonies, and by selecting the white colonies, the strains with substitution of NCgl1469 start codon through double crossover were finally selected. In addition, the sequence of selected strains was confirmed by PCR using a set of primers, NCgl1469-del-F1_BamHI and NCgl1469-del-R2_XbaI. The confirmed strain was named KCCM11138P NCgl1469(gtg).

Example 3

The Strain with Enhanced NCgl1469 Activity

Since it is known that the productivity of ornithine is increased in a mutant strain of ornithine-producing *Corynebacterium glutamicum* strain with enhanced NCgl1469 activity (Hwang et al., J Ind Microbiol Biotechnol, 37:11, 1131-1136, 2010), a polynucleotide encoding NCgl1469 was introduced in a form of plasmid or in a form to be inserted into the chromosome for increasing the ornithine productivity, and the effect thereof was analyzed.

Example 3-1

Cloning of the Gene Encoding NCgl1469 and Preparation of a Transformant with the Same In order to confirm the effect of increase in the copy number of NCgl1469 gene (including a promoter region) on high production of ornithine and putrescine, a mutant strain generated by introducing NCgl1469 in a form of plasmid into KCCM11138P strain described in Example 1.

To be specific, a polynucleotide encoding the NCgl1469 was amplified by PCR using NCgl1469 gene of ATCC13032 strain as a template and the primers (NCgl1469-300-F_KpnI and NCgl1469-R_XbaI) under the same condition as in Example 1. Through PCR, a gene fragment having a size of about 900 bp was obtained (Table 5).

TABLE 5

Primer to obtain the gene NCgl1469

| | |
|---|---|
| NCgl1469-300-F_KpnI (SEQ ID NO: 13) | CGGGGTACCTTCCAACGCTGCTATGAC |
| NCgl1469-R_XabI (SEQ ID NO: 14) | TGCTCTAGATTAAACAGTTGGCATCGCTGG |

The obtained gene fragments were restriction digested with KpnI and XbaI and cloned in to a pHC139T-gfp vector which was treated with the same restriction enzymes (Korean Patent No. 620092), thereby generating the expression vector, pHC139T-NCgl1469.

The prepared pHC139T-NCgl1469 vector was introduced to the strain KCCM11138P with the ability to produce putrescine in order to increase the productivity of ornithine and putrescine in a strain. The vector was introduced to the strain through electroporation, the transformed cells were plated on a BHIS medium plate containing 25 µg/ml kanamycin, and successful transformants were selected. The selected strain was named KCCM11138P/pHC139T-NCgl1469.

Example 3-2

The Mutant Strain with Chromosomal Insertion of the Gene Encoding NCgl1469

In order to confirm the effect of additional chromosomal insertion of NCgl1469 gene (including a promoter region) on high production of ornithine and putrescine, a mutant strain was generated by introducing NCgl1469 into the chromosome of KCCM11138P which was described in Example 1.

A vector pDZTn for transformation (Korean Publication No. 2008-0033054) which allows chromosomal insertion of a gene using the transposon gene location of microorganism of Corynebacterium genus was developed by the present inventors and it can be used in the same way as in the introduction of gene using a vector pDZ.

A gene fragment of NCgl1469 having a size of about 900 bp was obtained by PCR using the NCgl1469 gene of ATCC13032 strain as a template and a set of primers, NCgl1469-300-F_SpeI and NCgl1469-R_XhoI primers (Table 6).

TABLE 6

Primer II to obtain the gene NCgl1469

| NCgl1469-300-F_SpeI_Tn (SEQ ID NO: 15) | TGTCGGGCCCACTAGTTTCCAACG CTGCTCGGATGAC |
|---|---|
| NCgl1469-R_XhoI_Tn (SEQ ID NO: 16) | GAATGAGTTCCTCGAGTTAAACAG TTGGCATCGC |

The PCR reaction was performed with 30 cycles of denaturation at 95° C. for 40 seconds, annealing at 52° C. for 40 seconds, and elongation at 72° C. for 60 seconds using a pfu polymerase (Stratagene). After performing electrophoresis of the PCR products on 0.8% agarose gel, a DNA band of target size was isolated and purified. The purified gene fragment of NCgl1469 was fusion-cloned into a pDZTn vector which was restriction digested with SpeI&XhoI. For fusion cloning, In-Fusion HD Cloning Kit (Clontech) was used. The prepared plasmid was named as pDZTn-NCgl1469.

In order to obtain the KCCM111138P Tn::NCgl1469 strain, the prepared pDZ-NCgl1469 vector was introduced into KCCM11138P strain through electroporation and the transformed cells were plated on a BHIS medium plate containing kanamycin (25 µg/ml). Successful insertion of the vector to the chromosome was confirmed by the method described in Example 1 and through this, the strain inserted with the NCgl1469 gene in transposon gene position was selected. In addition, the sequence of mutant strain was confirmed by PCR using a set of primers, NCgl11469-300-F_SpeI_Tn and NCgl1469-R_XhoI_Tn. The confirmed strain was named as KCCM11138P Tn::NCgl1469.

Example 4

Comparison of the Ability of Producing Putrescine

In order to investigate the effects caused by deletion of NCgl1469 gene, substitution of start codon, enhancement of expression level, and chromosomal insertion of gene, the ability of the above-prepared strains for producing putrescine was evaluated.

To be specific, the prepared strains were cultured in a CM medium plate containing 1 mM arginine (glucose 1%, polypeptone 1%, yeast extract 0.5%, beef extract 0.5%, NaCl 0.25%, urea 0.2%, 50% NaOH 100 µl, agar 2%, pH 6.8 per 1 L) at 30° C. for 16 hours. Then, a loop of cell culture was inoculated in 25 ml of titer medium of Table 7 and cultured with shaking at 200 rpm at 30° C. for 96 hours. All of the prepared strains were cultured with addition of 1 mM arginine in the medium during fermentation.

TABLE 7

| Composition | Concentraton |
|---|---|
| Glucose | 5% |
| Soy Protein | 0.25% |
| Corn steep solids | 0.50% |
| $(NH_4)_2SO_4$ | 4% |
| Urea | 0.15% |
| $KH_2PO_4$ | 0.10% |
| $MgSO_4$ $7H_2O$ | 0.05% |
| Biotin | 100 µg |
| Thiamine Hydrochloride | 3000 µg |
| Calcium-Panthotenic Acid | 3000 µg |
| Nicotinamide | 3000 µg |
| $CaCO_3$ | 5% |

As a result, as shown in Table 8, when the function of NCgl1469 gene was inactivated by deletion the same in the putrescine-producing strain KCCM11138P, the N-acetyl putrescine was not produced. Also, the production level of putrescine was 2.6 g/L higher than the control group, demonstrating that the productivity of putrescine was increased in the strain by deletion of NCgl1469 gene.

In addition, when the function of NCgl1469 gene was weakened by substitution of the start codon of the same, the production level of N-acetyl putrescine, which was normally produced in a microorganism of KCCM11138P strain having the ability to produce putrescine, was decreased about 3 g/L as much. It is demonstrating that the productivity of N-acetyl putrescine was reduced by half.

Similar to KCCM11138P, when the function of NCgl1469 gene was inactivated by deletion of the same in the putrescine-producing strain DAB12-a derived from ATCC13869, N-acetyl putrescine was not produced, but the productivity of putrescine was improved.

These results showed that the pathway from putrescine to N-acetyl putrescine has been weakened or blocked by weakening or deleting NCgl1469 gene, and that the protein expressed from NCgl1469 gene acts to acetylate putrescine.

Meanwhile, when the activity of NCgl1469 was increased, the proportion of N-acetyl putrescine in the cell culture was higher than the control group, and there was no difference between gene expression in plasmid and additional chromosomal insertion of the gene in terms of the increase in the activity of NCgl11469.

When the activity of NCgl1469 gene was enhanced in general ornithine-producing strain, the conversion pathway from glutamate to acetyl glutamate was enhanced and production of ornithine was increased (Korean Patent Publication No. 2011-0080475). However, in the present invention, most of ornithine was converted to putrescine and therefore ornithine was not accumulated.

The difference in the results from a conventional method may be due to the fact that the protein expressed from NCgl1469 gene recognizes putrescine more easily than glutamate, and thus the production of N-acetyl putrescine was more enhanced than that of acetyl glutamate.

TABLE 8

| Strain type | Ornithine (g/L) | Putrescine (g/L) | N-Acetyl Putrescine (g/L) |
|---|---|---|---|
| KCCM11138P | 0 | 9.8 | 5.7 |
| KCCM11138P ΔNCgl1469 | 0 | 12.4 | 0.0 |
| KCCM11138P NCgl1469 (gtg) | 0 | 11.1 | 2.7 |
| KCCM11138P Tn::NCgl1469 | 0 | 5.8 | 9.8 |
| KCCM11138P/pHC139T | 0 | 9.5 | 6.1 |

TABLE 8-continued

| Strain type | Ornithine (g/L) | Putrescine (g/L) | N-Acetyl Putrescine (g/L) |
|---|---|---|---|
| KGCM11139P/pHC139T-NCgl1469 | 0 | 6.6 | 9.2 |
| DAB12-a | 0 | 10.1 | 6.3 |
| DAB12-a ΔNCgl1469 | 0 | 13.1 | 0.1 |

The present inventors have prepared the *Corynebacterium glutamicum* strain with increased productivity of putrescine without production of N-acetyl putrescine by deleting NCgl1469 gene in the transformed *Corynebacterium* sp. microorganism KCCM11138P having the ability of producing putrescine (Korean Patent Publication No. 2012-0064046) as described in Example 1-1, named this strain as *Corynebacterium glutamicum* CC01-0163, and deposited the same with the deposit number of KCCM11240P to Korean Culture Center of Microorganisms (hereinafter, referred to as "KCCM") having an address of 361-221, Yurim B/D, Hongje-l-dong, Seodaemun-gu, SEOUL 120-091, Republic of Korea, which is the international depositary authority under the Budapest Treaty in Dec. 26, 2011.

Based on the above descriptions, those skilled in the art will understand that the present invention can be conducted in other forms without changing the technical idea or essential technical features. In this regard, the Examples described above are to illustrate the invention in all respects, but not to limit the scope of the invention. It shall be understood that the scope of the present invention comprises any changes or modified forms derived from the meaning, scope and equivalent concept of the following claims rather than the detailed descriptions in the above.

The invention claimed is:

1. A recombinant microorganism of the genus *Corynebacterium* having enhanced ability to produce putrescine, wherein the acetyltransferase activity of a protein having the amino acid sequence of SEQ ID NO: 18 or SEQ ID NO: 20 in a microorganism of the genus *Corynebacterium* capable of producing putrescine is reduced or eliminated compared to the endogenous activity thereof by a mutation in an endogenous gene encoding the protein of SEQ ID NO: 18 or SEQ ID NO: 20.

2. The recombinant microorganism according to claim 1, wherein said microorganism of the genus *Corynebacterium* capable of producing putrescine has been modified to express an ornithine decarboxylase (ODC).

3. The recombinant microorganism according to claim 2, wherein the ODC has the amino acid sequence of SEQ ID NO: 23.

4. The recombinant microorganism according to claim 1, wherein the ornithine carbamoyltransferase (ArgF) activity and/or glutamate exporter (NCgl1221) activity are further reduced compared to the endogenous activity thereof, wherein said reduction in ornithine carbamoyltransferase activity is obtained by a mutation in an endogenous gene encoding ArgF, and wherein said reduction in glutamate exporter activity is obtained by a mutation in an endogenous gene encoding NCgl1221.

5. The recombinant microorganism according to claim 4, wherein ArgF has the amino acid sequence of SEQ ID NO: 21, and NCgl1221 has the amino acid sequence of SEQ ID NO: 22.

6. The recombinant microorganism according to claim 1, wherein the activity of at least one enzyme selected from the group consisting of acetyl gamma glutamyl phosphate reductase (ArgC), acetyl glutamate synthase or ornithine acetyltransferase (ArgJ), acetyl glutamate kinase (ArgB), and acetyl ornithine transferase (ArgD) is further enhanced by increasing the copy number of a gene encoding said enzyme, or by placing a gene encoding said enzyme under the control of a heterologous promoter.

7. The recombinant microorganism according to claim 6, wherein ArgC, ArgJ, ArgB and ArgD have the amino acid sequences of SEQ ID NOs: 24, 25, 26, and 27, respectively.

8. The recombinant microorganism according to claim 1, wherein said mutation is (a) a partial or whole deletion of the gene, (b) a mutation which reduces the expression of the gene, and/or (c) a mutation in the coding region of the gene.

9. The recombinant microorganism according to claim 1, wherein said recombinant microorganism of the genus *Corynebacterium* is *Corynebacterium glutamicum*.

10. A method for producing putrescine, comprising culturing a recombinant microorganism of the genus *Corynebacterium* having enhanced ability to produce putrescine, wherein the acetyltransferase activity of a protein having the amino acid sequence of SEQ ID NO: 18 or SEQ ID NO: 20 in a microorganism of the genus *Corynebacterium* capable of producing putrescine is reduced or eliminated compared to the endogenous activity thereof by a mutation in an endogenous gene encoding the protein of SEQ ID NO: 18 or SEQ ID NO: 20; and isolating putrescine from the cell culture.

11. The method for producing putrescine according to claim 10, wherein said recombinant microorganism of the genus *Corynebacterium* is *Corynebacterium glutamicum*.

* * * * *

SEQUENCE LISTING

<160> NUMBER OF SEQ ID NOS: 27

<210> SEQ ID NO 1
<211> LENGTH: 28
<212> TYPE: DNA
<213> ORGANISM: Artificial Sequence
<220> FEATURE:
<223> OTHER INFORMATION: Primer

<400> SEQUENCE: 1
cgggatccaa ccttcagaac gcgaatac                                    28

<210> SEQ ID NO 2
<211> LENGTH: 29
<212> TYPE: DNA
<213> ORGANISM: Artificial Sequence
<220> FEATURE:
<223> OTHER INFORMATION: Primer

<400> SEQUENCE: 2
cgcgtcgact tggcactgtg attaccatc                                   29

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
cgcgtcgact tgggttatat cccctcaga                                   29

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
tgctctagat agtgagccaa gacatggaa                                   29

<210> SEQ ID NO 5
<211> LENGTH: 24
<212> TYPE: DNA
<213> ORGANISM: Artificial Sequence
<220> FEATURE:
<223> OTHER INFORMATION: Primer -continued

```
<400> SEQUENCE: 5
catcctgggg aattcatttg tcat                                              24

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
ggcgttcgac aaagcctaat aag                                               23

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
cgggatccgt ggctgccagg aatggctcc                                         29

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
tgctctagac ccaaaacatc ctggcggc                                          28

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
cgggatcctg cattgtatac tgcgaccac                                         29

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
caaaacggtg ggactcacgg ataccagaat agc                                    33

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
gctattctgg tatccgtgag tcccaccgtt ttg                                    33

<210> SEQ ID NO 12
```

```
<211> LENGTH: 30
<212> TYPE: DNA
<213> ORGANISM: Artificial Sequence
<220> FEATURE:
<223> OTHER INFORMATION: Primer

<400> SEQUENCE: 12
tgctctagat taaacagttg gcatcgctgg                                        30

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
cggggtacct tccaacgctg ctcggatgac                                        30

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
tgctctagat taaacagttg gcatcgctgg                                        30

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
tgtcgggccc actagtttcc aacgctgctc ggatgac                                37

<210> SEQ ID NO 16
<211> LENGTH: 37
<212> TYPE: DNA
<213> ORGANISM: Artificial Sequence
<220> FEATURE:
<223> OTHER INFORMATION: Primer

<400> SEQUENCE: 16
gaatgagttc ctcgagttaa acagttggca tcgctgg                                37

<210> SEQ ID NO 17
<211> LENGTH: 612
<212> TYPE: DNA
<213> ORGANISM: Corynebacterium glutamicum

<400> SEQUENCE: 17
atgagtccca ccgttttgcc tgctacacaa gctgacttcc ctaagatcgt cgatgttctg       60
gttgaagcat cgccaacga tccagcattt ttacgatgga tcccgcagcc ggaccccggt      120
tcagcaaagc ttcgagcact tttcgaactg cagattgaga agcagtatgc agtggcggga      180
aatattgatg tcgcgcgtga ttctgaggga gaaatcgtcg gcgtcgcgtt atgggatcgg      240
ccagatggta atcacagtgc caaagatcaa gcagcgatgc tccccggct cgtctccatt      300 ttcgggatca aggctgcgca ggtggcgtgg acgatttga gttcggctcg tttccacccc      360
aaattccccc attggtacct ctacaccgtg gcaacatcta gttctgcccg tggaacgggt      420
```

```
gttggcagtg cgcttcttaa tcacggaatc gctcgcgcgg gtgatgaagc tatctatttg    480
gaggcgacgt cgactcgtgc ggctcaacta tataaccgtc tgggatttgt gcccttgggt    540
tatatcccct cagatgatga tggcactcct gaactggcga tgtggaaacc gccagcgatg    600
ccaactgttt aa                                                        612

<210> SEQ ID NO 18
<211> LENGTH: 203
<212> TYPE: PRT
<213> ORGANISM: Corynebacterium glutamicum

<400> SEQUENCE: 18

Met Ser Pro Thr Val Leu Pro Ala Thr Gln Ala Asp Phe Pro Lys Ile
 1               5                  10                  15

Val Asp Val Leu Val Glu Ala Phe Ala Asn Asp Pro Ala Phe Leu Arg
            20                  25                  30

Trp Ile Pro Gln Pro Asp Pro Gly Ser Ala Lys Leu Arg Ala Leu Phe
        35                  40                  45

Glu Leu Gln Ile Glu Lys Gln Tyr Ala Val Ala Gly Asn Ile Asp Val
    50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Met Leu Pro Arg
                85                  90                  95

Leu Val Ser Ile Phe Gly Ile Lys Ala Ala Gln Val Ala Trp Thr Asp
            100                 105                 110

Leu Ser Ser Ala Arg Phe His Pro Lys Phe Pro His Trp Tyr Leu Tyr
        115                 120                 125

Thr Val Ala Thr Ser Ser Ala Arg Gly Thr Gly Val Gly Ser Ala
    130                 135                 140

Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                165                 170                 175

Val Pro Leu Gly Tyr Ile Pro Ser Asp Asp Gly Thr Pro Glu Leu
            180                 185                 190

Ala Met Trp Lys Pro Pro Ala Met Pro Thr Val
        195                 200

<210> SEQ ID NO 19
<211> LENGTH: 612
<212> TYPE: DNA
<213> ORGANISM: Corynebacterium glutamicum

<400> SEQUENCE: 19
atgagtccca ccgttttgcc tgctacacaa gctgacttcc ctaagatcgt cgatgttctg     60
gttgaagcat tcgccaacga tccagcattt ttacgatgga tcccgcagcc ggaccccggt    120
tcagcaaagc ttcgagcact tttcgaactg cagattgaga agcagtatgc agtggcggga    180
aatattgatg tcgcgcgtga ttctgaggga gaaatcgtcg gcgtcgcgtt atgggatcgg    240
ccagatggta atcacagtgc aaagatcaa gcagcgatac tccccggct cgtctccatt    300 ttcgggatca aggctgcgca ggtggcgtgg acggatttga gttcggctcg tttccacccc    360
aaattccccc attggtacct ctacaccgtg gcaaatcta gttctgcccg tggaacgggt    420
gttggcagtg cgcttcttaa tcacggaatc gctcgcgcgg gtgatgaagc tatctatttg    480
```

-continued

```
gaggcgacgt cgactcgtgc ggctcaacta tataaccgtc tgggatttgt gcccttgggt    540
tatatcccct cagatgatga tggcactcct gaactggcga tgtggaaacc gccagcgatg    600
ccaactgttt aa                                                       612
```

<210> SEQ ID NO 20
<211> LENGTH: 203
<212> TYPE: PRT
<213> ORGANISM: Corynebacterium glutamicum

<400> SEQUENCE: 20

| Met | Ser | Pro | Thr | Val | Leu | Pro | Ala | Thr | Gln | Ala | Asp | Phe | Pro | Lys | Ile |
|---|---|---|---|---|---|---|---|---|---|---|---|---|---|---|---|
| 1 | | | | 5 | | | | | 10 | | | | | 15 | |

| Val | Asp | Val | Leu | Val | Glu | Ala | Phe | Ala | Asn | Asp | Pro | Ala | Phe | Leu | Arg |
| | | | 20 | | | | | 25 | | | | | 30 | | |

| Trp | Ile | Pro | Gln | Pro | Asp | Pro | Gly | Ser | Ala | Lys | Leu | Arg | Ala | Leu | Phe |
| | | | 35 | | | | | 40 | | | | | 45 | | |

| Glu | Leu | Gln | Ile | Glu | Lys | Gln | Tyr | Ala | Val | Ala | Gly | Asn | Ile | Asp | Val |
| | 50 | | | | | 55 | | | | | 60 | | | | |

| Ala | Arg | Asp | Ser | Glu | Gly | Glu | Ile | Val | Gly | Val | Ala | Leu | Trp | Asp | Arg |
| 65 | | | | | 70 | | | | | 75 | | | | | 80 |

| Pro | Asp | Gly | Asn | His | Ser | Ala | Lys | Asp | Gln | Ala | Ala | Ile | Leu | Pro | Arg |
| | | | | 85 | | | | | 90 | | | | | 95 | |

| Leu | Val | Ser | Ile | Phe | Gly | Ile | Lys | Ala | Ala | Gln | Val | Ala | Trp | Thr | Asp |
| | | | 100 | | | | | 105 | | | | | 110 | | |

| Leu | Ser | Ser | Ala | Arg | Phe | His | Pro | Lys | Phe | Pro | His | Trp | Tyr | Leu | Tyr |
| | | 115 | | | | | 120 | | | | | 125 | | | |

| Thr | Val | Ala | Thr | Ser | Ser | Ala | Arg | Gly | Thr | Gly | Val | Gly | Ser | Ala |
| | 130 | | | | | 135 | | | | | 140 | | | | |

| Leu | Leu | Asn | His | Gly | Ile | Ala | Arg | Ala | Gly | Asp | Glu | Ala | Ile | Tyr | Leu |
| 145 | | | | | 150 | | | | | 155 | | | | | 160 |

| Glu | Ala | Thr | Ser | Thr | Arg | Ala | Ala | Gln | Leu | Tyr | Asn | Arg | Leu | Gly | Phe |
| | | | | 165 | | | | | 170 | | | | | 175 | |

| Val | Pro | Leu | Gly | Tyr | Ile | Pro | Ser | Asp | Asp | Asp | Gly | Thr | Pro | Glu | Leu |
| | | | 180 | | | | | 185 | | | | | 190 | | |

| Ala | Met | Trp | Lys | Pro | Pro | Ala | Met | Pro | Thr | Val |
| | | | 195 | | | | | 200 | | |

<210> SEQ ID NO 21
<211> LENGTH: 319
<212> TYPE: PRT
<213> ORGANISM: Corynebacterium glutamicum

<400> SEQUENCE: 21

| Met | Thr | Ser | Gln | Pro | Gln | Val | Arg | His | Phe | Leu | Ala | Asp | Asp | Leu |
| 1 | | | | 5 | | | | | 10 | | | | | 15 |

| Thr | Pro | Ala | Glu | Gln | Ala | Glu | Val | Leu | Thr | Leu | Ala | Ala | Lys | Leu | Lys |
| | | | 20 | | | | | 25 | | | | | 30 | | |

| Ala | Ala | Pro | Phe | Ser | Glu | Arg | Pro | Leu | Glu | Gly | Pro | Lys | Ser | Val | Ala |
| | | | 35 | | | | | 40 | | | | | 45 | | |

| Val | Leu | Phe | Asp | Lys | Thr | Ser | Thr | Arg | Thr | Arg | Phe | Ser | Phe | Asp | Ala |
| | 50 | | | | | 55 | | | | | 60 | | | | |

| Gly | Ile | Ala | His | Leu | Gly | Gly | His | Ala | Ile | Val | Val | Asp | Ser | Gly | Ser |
| 65 | | | | | 70 | | | | | 75 | | | | | 80 |

| Ser | Gln | Met | Gly | Lys | Gly | Glu | Ser | Leu | Gln | Asp | Thr | Ala | Ala | Val | Leu |
| | | | | 85 | | | | | 90 | | | | | 95 | |

Ser Arg Tyr Val Glu Ala Ile Val Trp Arg Thr Tyr Ala His Ser Asn
            100                 105                 110

Phe His Ala Met Ala Glu Thr Ser Thr Val Pro Leu Val Asn Ser Leu
        115                 120                 125

Ser Asp Asp Leu His Pro Cys Gln Ile Leu Ala Asp Leu Gln Thr Ile
130                 135                 140

Val Glu Asn Leu Ser Pro Glu Glu Gly Pro Ala Gly Leu Lys Gly Lys
145                 150                 155                 160

Lys Ala Val Tyr Leu Gly Asp Gly Asp Asn Asn Met Ala Asn Ser Tyr
                165                 170                 175

Met Ile Gly Phe Ala Thr Ala Gly Met Asp Ile Ser Ile Ala Pro
            180                 185                 190

Glu Gly Phe Gln Pro Arg Ala Glu Phe Val Glu Arg Ala Glu Lys Arg
        195                 200                 205

Gly Gln Glu Thr Gly Ala Lys Val Val Thr Asp Ser Leu Asp Glu
210                 215                 220

Val Ala Gly Ala Asp Val Val Ile Thr Asp Thr Trp Val Ser Met Gly
225                 230                 235                 240

Met Glu Asn Asp Gly Ile Asp Arg Thr Thr Pro Phe Val Pro Tyr Gln
                245                 250                 255

Val Asn Asp Glu Val Met Ala Lys Ala Asn Asp Gly Ala Ile Phe Leu
            260                 265                 270

His Cys Leu Pro Ala Tyr Arg Gly Lys Glu Val Ala Ala Ser Val Ile
        275                 280                 285

Asp Gly Pro Ala Ser Lys Val Phe Asp Glu Ala Glu Asn Arg Leu His
290                 295                 300

Ala Gln Lys Ala Leu Leu Val Trp Leu Leu Ala Asn Gln Pro Arg
305                 310                 315

<210> SEQ ID NO 22
<211> LENGTH: 533
<212> TYPE: PRT
<213> ORGANISM: Corynebacterium glutamicum

<400> SEQUENCE: 22

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Arg
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Phe Gly Phe Ser Leu Ala Gly Ala
                85                  90                  95

Ala Ile Pro Ala Thr Ile Ala Ser Ala Ile Gly Leu Gly Ala Gln
            100                 105                 110

Ser Ile Val Ala Asp Phe Leu Ala Gly Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg

```
            145                 150                 155                 160
Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
                260                 265                 270

Ile Ile Ser Glu Phe Trp Glu Glu Tyr Gly Ser Ala Thr Thr Thr Ser
            275                 280                 285

Gly Thr Leu Ile Asp Ser Leu His Val Glu His Glu Glu Pro Lys Thr
        290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Val Ile Asn Ala Gly Asn Pro Glu Lys Glu
                340                 345                 350

Leu Asp Ser Asp Val Leu Glu Gln Glu Leu Ser Ser Glu Glu Pro Glu
        355                 360                 365

Glu Thr Ala Lys Pro Asp His Ser Leu Arg Gly Phe Phe Arg Thr Asp
370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
                420                 425                 430

Gly Trp Leu Ser Pro Ser Thr Ala Thr Ser Thr Ala Val Thr Thr Ser
        435                 440                 445

Glu Thr Ser Ala Pro Val Ser Thr Pro Ser Met Thr Val Pro Thr Thr
450                 455                 460

Val Glu Glu Thr Pro Thr Met Glu Ser Asn Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
            500                 505                 510

Gln Ser Pro Ala Val Glu Ala Pro Thr Ala Val Gln Glu Thr Val Ala
        515                 520                 525

Pro Thr Ser Thr Pro
        530

<210> SEQ ID NO 23
<211> LENGTH: 711
<212> TYPE: PRT
<213> ORGANISM: Corynebacterium glutamicum
```

<400> SEQUENCE: 23

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ile His Glu Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
        275                 280                 285

Val Tyr Asn Ala Arg Gln Val Ile Asp Thr Val Gly His Leu Cys Asp
    290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
            340                 345                 350

Ser Gln Thr Ser Gln Ile His Lys Lys Asp Asn His Ile Arg Gly Gln
        355                 360                 365

Ala Arg Phe Cys Pro His Lys Arg Leu Asn Asn Ala Phe Met Leu His
    370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys

```
                    405                 410                 415
Val Glu Ile Gly Ile Glu Ala Arg Lys Ala Ile Leu Ala Arg Cys Lys
            420                 425                 430

Leu Phe Arg Pro Phe Ile Pro Pro Val Val Asp Gly Lys Leu Trp Gln
            435                 440                 445

Asp Tyr Pro Thr Ser Val Leu Ala Ser Asp Arg Arg Phe Phe Ser Phe
            450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
            515                 520                 525

Asn Ser Ile Leu Phe Leu Leu Thr Pro Ala Glu Ser His Glu Lys Leu
530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
            595                 600                 605

Arg Gln Gln Ser Phe Pro Ser Val Val Met Asn Pro Gln Asp Ala His
            610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
            660                 665                 670

Phe Leu Ala Leu Glu Glu Gly Val Asn Leu Leu Pro Gly Phe Ser Pro
            675                 680                 685

Glu Leu Gln Gly Val Tyr Ser Glu Thr Asp Ala Asp Gly Val Lys Arg
            690                 695                 700

Leu Tyr Gly Tyr Val Leu Lys
705                 710

<210> SEQ ID NO 24
<211> LENGTH: 357
<212> TYPE: PRT
<213> ORGANISM: Corynebacterium glutamicum

<400> SEQUENCE: 24

Met Ile Met His Asn Val Tyr Gly Val Thr Met Thr Ile Lys Val Ala
  1               5                  10                  15

Ile Ala Gly Ala Ser Gly Tyr Ala Gly Gly Glu Ile Leu Arg Leu Leu
            20                  25                  30

Leu Gly His Pro Ala Tyr Ala Ser Gly Glu Leu Glu Ile Gly Ala Leu
        35                  40                  45

Thr Ala Ala Ser Thr Ala Gly Ser Thr Leu Gly Glu Leu Met Pro His
    50                  55                  60
```

-continued

```
Ile Pro Gln Leu Ala Asp Arg Val Ile Gln Asp Thr Thr Ala Glu Thr
 65                  70                  75                  80

Leu Ala Gly His Asp Val Val Phe Leu Gly Leu Pro His Gly Phe Ser
                 85                  90                  95

Ala Glu Ile Ala Leu Gln Leu Gly Pro Asp Val Thr Val Ile Asp Cys
            100                 105                 110

Ala Ala Asp Phe Arg Leu Gln Asn Ala Ala Asp Trp Glu Lys Phe Tyr
        115                 120                 125

Gly Ser Glu His Gln Gly Thr Trp Pro Tyr Gly Ile Pro Glu Met Pro
    130                 135                 140

Gly His Arg Glu Ala Leu Arg Gly Ala Lys Arg Val Ala Val Pro Gly
145                 150                 155                 160

Cys Phe Pro Thr Gly Ala Thr Leu Ala Leu Leu Pro Ala Val Gln Ala
                165                 170                 175

Gly Leu Ile Glu Pro Asp Val Ser Val Val Ser Ile Thr Gly Val Ser
            180                 185                 190

Gly Ala Gly Lys Lys Ala Ser Val Ala Leu Leu Gly Ser Glu Thr Met
        195                 200                 205

Gly Ser Leu Lys Ala Tyr Asn Thr Ser Gly Lys His Arg His Thr Pro
    210                 215                 220

Glu Ile Ala Gln Asn Leu Gly Glu Val Ser Asp Lys Pro Val Lys Val
225                 230                 235                 240

Ser Phe Thr Pro Val Leu Ala Pro Leu Pro Arg Gly Ile Leu Thr Thr
                245                 250                 255

Ala Thr Ala Pro Leu Lys Glu Gly Val Thr Ala Glu Gln Ala Arg Ala
            260                 265                 270

Val Tyr Glu Glu Phe Tyr Ala Gln Glu Thr Phe Val His Val Leu Pro
        275                 280                 285

Glu Gly Ala Gln Pro Gln Thr Gln Ala Val Leu Gly Ser Asn Met Cys
    290                 295                 300

His Val Gln Val Glu Ile Asp Glu Glu Ala Gly Lys Val Leu Val Thr
305                 310                 315                 320

Ser Ala Ile Asp Asn Leu Thr Lys Gly Thr Ala Gly Ala Ala Val Gln
                325                 330                 335

Cys Met Asn Leu Ser Val Gly Phe Asp Glu Ala Ala Gly Leu Pro Gln
            340                 345                 350

Val Gly Val Ala Pro
        355

<210> SEQ ID NO 25
<211> LENGTH: 388
<212> TYPE: PRT
<213> ORGANISM: Corynebacterium glutamicum

<400> SEQUENCE: 25

Met Ala Glu Lys Gly Ile Thr Ala Pro Lys Gly Phe Val Ala Ser Ala
  1               5                  10                  15

Thr Thr Ala Gly Ile Lys Ala Ser Gly Asn Pro Asp Met Ala Leu Val
                 20                  25                  30

Val Asn Gln Gly Pro Glu Phe Ser Ala Ala Val Phe Thr Arg Asn
             35                  40                  45

Arg Val Phe Ala Ala Pro Val Lys Val Ser Arg Glu Asn Val Ala Asp
         50                  55                  60

Gly Gln Ile Arg Ala Val Leu Tyr Asn Ala Gly Asn Ala Asn Ala Cys
 65                  70                  75                  80
```

-continued

```
Asn Gly Leu Gln Gly Glu Lys Asp Ala Arg Glu Ser Val Ser His Leu
             85                  90                  95

Ala Gln Asn Leu Gly Leu Glu Asp Ser Asp Ile Gly Val Cys Ser Thr
            100                 105                 110

Gly Leu Ile Gly Glu Leu Leu Pro Met Asp Lys Leu Asn Ala Gly Ile
        115                 120                 125

Asp Gln Leu Thr Ala Glu Gly Ala Leu Gly Asp Asn Gly Ala Ala Ala
    130                 135                 140

Ala Lys Ala Ile Met Thr Thr Asp Thr Val Asp Lys Glu Thr Val Val
145                 150                 155                 160

Phe Ala Asp Gly Trp Thr Val Gly Gly Met Gly Lys Gly Val Gly Met
                165                 170                 175

Met Ala Pro Ser Leu Ala Thr Met Leu Val Cys Leu Thr Thr Asp Ala
            180                 185                 190

Ser Val Thr Gln Glu Met Ala Gln Ile Ala Leu Ala Asn Ala Thr Ala
        195                 200                 205

Val Thr Phe Asp Thr Leu Asp Ile Asp Gly Ser Thr Ser Thr Asn Asp
    210                 215                 220

Thr Val Phe Leu Leu Ala Ser Gly Ala Ser Gly Ile Thr Pro Thr Gln
225                 230                 235                 240

Asp Glu Leu Asn Asp Ala Val Tyr Ala Ala Cys Ser Asp Ile Ala Ala
                245                 250                 255

Lys Leu Gln Ala Asp Ala Glu Gly Val Thr Lys Arg Val Ala Val Thr
            260                 265                 270

Val Val Gly Thr Thr Asn Asn Glu Gln Ala Ile Asn Ala Ala Arg Thr
        275                 280                 285

Val Ala Arg Asp Asn Leu Phe Lys Cys Ala Met Phe Gly Ser Asp Pro
    290                 295                 300

Asn Trp Gly Arg Val Leu Ala Ala Val Gly Met Ala Asp Ala Asp Met
305                 310                 315                 320

Glu Pro Glu Lys Ile Ser Val Phe Asn Gly Gln Ala Val Cys Leu
                325                 330                 335

Asp Ser Thr Gly Ala Pro Gly Ala Arg Glu Val Asp Leu Ser Gly Ala
            340                 345                 350

Asp Ile Asp Val Arg Ile Asp Leu Gly Thr Ser Gly Glu Gly Gln Ala
        355                 360                 365

Thr Val Arg Thr Thr Asp Leu Ser Phe Ser Tyr Val Glu Ile Asn Ser
    370                 375                 380

Ala Tyr Ser Ser
385

<210> SEQ ID NO 26
<211> LENGTH: 317
<212> TYPE: PRT
<213> ORGANISM: Corynebacterium glutamicum

<400> SEQUENCE: 26

Met Asn Asp Leu Ile Lys Asp Leu Gly Ser Glu Val Arg Ala Asn Val
  1               5                  10                  15

Leu Ala Glu Ala Leu Pro Trp Leu Gln His Phe Arg Asp Lys Ile Val
             20                  25                  30

Val Val Lys Tyr Gly Gly Asn Ala Met Val Asp Asp Asp Leu Lys Ala
         35                  40                  45

Ala Phe Ala Ala Asp Met Val Phe Leu Arg Thr Val Gly Ala Lys Pro
```

```
            50                  55                  60
Val Val Val His Gly Gly Pro Gln Ile Ser Glu Met Leu Asn Arg
 65                  70                  75                  80

Val Gly Leu Gln Gly Glu Phe Lys Gly Gly Phe Arg Val Thr Thr Pro
                 85                  90                  95

Glu Val Met Asp Ile Val Arg Met Val Leu Phe Gly Gln Val Gly Arg
                100                 105                 110

Asp Leu Val Gly Leu Ile Asn Ser His Gly Pro Tyr Ala Val Gly Thr
                115                 120                 125

Ser Gly Glu Asp Ala Gly Leu Phe Thr Ala Gln Lys Arg Met Val Asn
                130                 135                 140

Ile Asp Gly Val Pro Thr Asp Ile Gly Leu Val Gly Asp Ile Ile Asn
145                 150                 155                 160

Val Asp Ala Ser Ser Leu Met Asp Ile Ile Glu Ala Gly Arg Ile Pro
                165                 170                 175

Val Val Ser Thr Ile Ala Pro Gly Glu Asp Gly Gln Ile Tyr Asn Ile
                180                 185                 190

Asn Ala Asp Thr Ala Ala Gly Ala Leu Ala Ala Ile Gly Ala Glu
                195                 200                 205

Arg Leu Leu Val Leu Thr Asn Val Glu Gly Leu Tyr Thr Asp Trp Pro
210                 215                 220

Asp Lys Ser Ser Leu Val Ser Lys Ile Lys Ala Thr Glu Leu Glu Ala
225                 230                 235                 240

Ile Leu Pro Gly Leu Asp Ser Gly Met Ile Pro Lys Met Glu Ser Cys
                245                 250                 255

Leu Asn Ala Val Arg Gly Gly Val Ser Ala Ala His Val Ile Asp Gly
                260                 265                 270

Arg Ile Ala His Ser Val Leu Leu Glu Leu Leu Thr Met Gly Gly Ile
                275                 280                 285

Gly Thr Met Val Leu Pro Asp Val Phe Asp Arg Glu Asn Tyr Pro Glu
                290                 295                 300

Gly Thr Val Phe Arg Lys Asp Lys Asp Gly Glu Leu
305                 310                 315

<210> SEQ ID NO 27
<211> LENGTH: 391
<212> TYPE: PRT
<213> ORGANISM: Corynebacterium glutamicum

<400> SEQUENCE: 27

Met Ser Thr Leu Glu Thr Trp Pro Gln Val Ile Ile Asn Thr Tyr Gly
  1               5                  10                  15

Thr Pro Pro Val Glu Leu Val Ser Gly Lys Gly Ala Thr Val Thr Asp
                 20                  25                  30

Asp Gln Gly Asn Val Tyr Ile Asp Leu Leu Ala Gly Ile Ala Val Asn
                 35                  40                  45

Ala Leu Gly His Ala His Pro Ala Ile Ile Glu Ala Val Thr Asn Gln
                 50                  55                  60

Ile Gly Gln Leu Gly His Val Ser Asn Leu Phe Ala Ser Arg Pro Val
 65                  70                  75                  80

Val Glu Val Ala Glu Glu Leu Ile Lys Arg Phe Ser Leu Asp Asp Ala
                 85                  90                  95

Thr Leu Ala Ala Gln Thr Arg Val Phe Phe Cys Asn Ser Gly Ala Glu
                100                 105                 110
```

```
Ala Asn Glu Ala Ala Phe Lys Ile Ala Arg Leu Thr Gly Arg Ser Arg
    115                 120                 125

Ile Leu Ala Ala Val His Gly Phe His Gly Arg Thr Met Gly Ser Leu
    130                 135                 140

Ala Leu Thr Gly Gln Pro Asp Lys Arg Glu Ala Phe Leu Pro Met Pro
145             150                 155                 160

Ser Gly Val Glu Phe Tyr Pro Tyr Gly Asp Thr Asp Tyr Leu Arg Lys
                165                 170                 175

Met Val Glu Thr Asn Pro Thr Asp Val Ala Ala Ile Phe Leu Glu Pro
            180                 185                 190

Ile Gln Gly Glu Thr Gly Val Val Pro Ala Pro Glu Gly Phe Leu Lys
        195                 200                 205

Ala Val Arg Glu Leu Cys Asp Glu Tyr Gly Ile Leu Met Ile Thr Asp
    210                 215                 220

Glu Val Gln Thr Gly Val Gly Arg Thr Gly Asp Phe Phe Ala His Gln
225             230                 235                 240

His Asp Gly Val Val Pro Asp Val Val Thr Met Ala Lys Gly Leu Gly
                245                 250                 255

Gly Gly Leu Pro Ile Gly Ala Cys Leu Ala Thr Gly Arg Ala Ala Glu
            260                 265                 270

Leu Met Thr Pro Gly Lys His Gly Thr Thr Phe Gly Gly Asn Pro Val
        275                 280                 285

Ala Cys Ala Ala Ala Lys Ala Val Leu Ser Val Val Asp Asp Ala Phe
    290                 295                 300

Cys Ala Glu Val Ala Arg Lys Gly Glu Leu Phe Lys Glu Leu Leu Ala
305             310                 315                 320

Lys Val Asp Gly Val Val Asp Val Arg Gly Arg Gly Leu Met Leu Gly
                325                 330                 335

Val Val Leu Glu Arg Asp Val Ala Lys Gln Ala Val Leu Asp Gly Phe
            340                 345                 350

Lys His Gly Val Ile Leu Asn Ala Pro Ala Asp Asn Ile Ile Arg Leu
        355                 360                 365

Thr Pro Pro Leu Val Ile Thr Asp Glu Glu Ile Ala Asp Ala Val Lys
    370                 375                 380

Ala Ile Ala Glu Thr Ile Ala
385             390
```